(12) United States Patent
Rudman

(10) Patent No.: US 10,271,926 B2
(45) Date of Patent: Apr. 30, 2019

(54) POCKET ORTHODONTIC BONDING PAD

(71) Applicant: Robert T. Rudman, Denver, CO (US)

(72) Inventor: Robert T. Rudman, Denver, CO (US)

(*) Notice: Subject to any disclaimer, the term of this patent is extended or adjusted under 35 U.S.C. 154(b) by 0 days.

(21) Appl. No.: 15/864,895

(22) Filed: Jan. 8, 2018

(65) Prior Publication Data

US 2018/0153654 A1 Jun. 7, 2018

Related U.S. Application Data

(62) Division of application No. 14/738,748, filed on Jun. 12, 2015, now Pat. No. 9,883,924.

(60) Provisional application No. 62/011,423, filed on Jun. 12, 2014.

(51) Int. Cl.
| | |
|---|---|
| A61C 7/00 | (2006.01) |
| A61C 7/16 | (2006.01) |
| A61C 7/14 | (2006.01) |
| A61C 13/00 | (2006.01) |
| A61C 7/02 | (2006.01) |

(52) U.S. Cl.
CPC ............. *A61C 7/16* (2013.01); *A61C 7/002* (2013.01); *A61C 7/14* (2013.01); *A61C 7/146* (2013.01); *A61C 7/023* (2013.01); *A61C 7/141* (2013.01); *A61C 13/0013* (2013.01)

(58) Field of Classification Search
CPC ........... A61C 7/16; A61C 7/146; A61C 7/023; A61C 7/141; A61C 7/14; A61C 7/287
See application file for complete search history.

(56) References Cited

U.S. PATENT DOCUMENTS

| | | |
|---|---|---|
| 3,421,221 A | 1/1969 | Silverman et al. |
| 3,461,559 A | 8/1969 | Silverman |
| 3,946,488 A | 3/1976 | Miller |
| 4,355,975 A | 10/1982 | Fujita |
| 4,369,033 A | 1/1983 | Webb et al. |
| 4,597,739 A | 7/1986 | Rosenberg |
| 5,098,288 A | 3/1992 | Kesling |

(Continued)

FOREIGN PATENT DOCUMENTS

| | | |
|---|---|---|
| GB | 687226 | 2/1953 |
| KR | 20100077765 | 7/2010 |

(Continued)

OTHER PUBLICATIONS

Dan Grauer, et al., "Computer-Aided Design/Computer-Aided Manufacturing Technology in Customized Orthodontic Appliances," 24 J. Esthetic & Restorative Dentistry 3 (2012).

(Continued)

*Primary Examiner* — Paula J Stice
(74) *Attorney, Agent, or Firm* — Amin Talati Upadhye LLP; Joseph E. Cwik; Adam D. Sussman

(57) ABSTRACT

A pocket orthodontic bonding pad for attaching orthodontic attachments to teeth wherein the orthodontic attachment is mechanically secured within a bonding pad pocket with a design that allows a slight buffering flexibility under masticatory stress and ease of removal of the orthodontic attachment. Upon removal of locking tabs the orthodontic attachment may be removed with minimal force, and the remaining bonding pad polished from the teeth with ease, which is most advantageous for brackets that tend to break upon removal and create high stress forces upon tooth structure. The ease of removing orthodontic attachments allows maximum bonding strengths.

15 Claims, 12 Drawing Sheets

(56) References Cited

U.S. PATENT DOCUMENTS

| | | |
|---|---|---|
| 5,263,859 A | 11/1993 | Kesling |
| 5,542,844 A | 8/1996 | Perret, Jr. |
| 6,685,468 B1 | 2/2004 | Kesling |
| 6,746,242 B1 | 6/2004 | Kesling |
| 7,131,836 B1 | 11/2006 | Kesling |
| 7,188,421 B2 | 3/2007 | Cleary |
| 7,331,782 B2 | 2/2008 | Andreiko |
| 7,780,442 B2 | 8/2010 | Kesling |
| 7,819,660 B2 | 10/2010 | Cosse |
| 8,152,519 B1 | 4/2012 | Dumas |
| 8,235,717 B2 | 8/2012 | Kuperman |
| 8,550,814 B1 | 10/2013 | Collins |
| 8,552,086 B2 | 10/2013 | Karim |
| 8,690,568 B2 | 4/2014 | Chapoulaud |
| 8,696,705 B2 | 4/2014 | Hakim |
| 8,992,215 B2 | 3/2015 | Chapoulaud |
| 2003/0198913 A1 | 10/2003 | Cindader et al. |
| 2007/0111152 A1 | 5/2007 | Primus et al. |
| 2007/0196790 A1 | 8/2007 | Cosse |
| 2007/0259302 A1 | 11/2007 | Jayawardena |
| 2011/0311933 A1 | 12/2011 | Parker |
| 2013/0323666 A1 | 12/2013 | Vu |
| 2014/0065568 A1 | 3/2014 | Rahimi |
| 2014/0141383 A1 | 5/2014 | Hagelganz et al. |
| 2014/0255865 A1 | 9/2014 | Gautam |

FOREIGN PATENT DOCUMENTS

| | | |
|---|---|---|
| KR | 20130125132 | 11/2013 |
| WO | 03/059186 A1 | 7/2003 |
| WO | 2011/013903 A2 | 2/2011 |

OTHER PUBLICATIONS

Dirk Weichmann, et al., "Customized brackets and archwires for lingual orthodontic treatment," 124 Am. J. Orthodontics & Dentofacial Orthopedics 593 (2003).

Neal D. Kravitz, et al., "Intraoral Digital Scanners," 48 J. Clinical Orthodontics 337 (2014).

Christian Groth, et al., "Three-Dimensional Printing Technology," 48 J. Clinical Orthodontics 475 (2014).

C.B. Martin, et al., "Orthodontic scanners: what's available?," 42 J. Orthodontics 136 (2015).

Emilia Taneva, et al., "3D Scanning, Imaging, and Printing in Orthodontics," in Issues in Contemporary Orthodontics 147 (IntechOpen 2015).

Neal D. Kravitz, et al., "CAD/CAM Software for Three-Dimensional Printing," 52 J. Clinical Orthodontics 22 (2018).

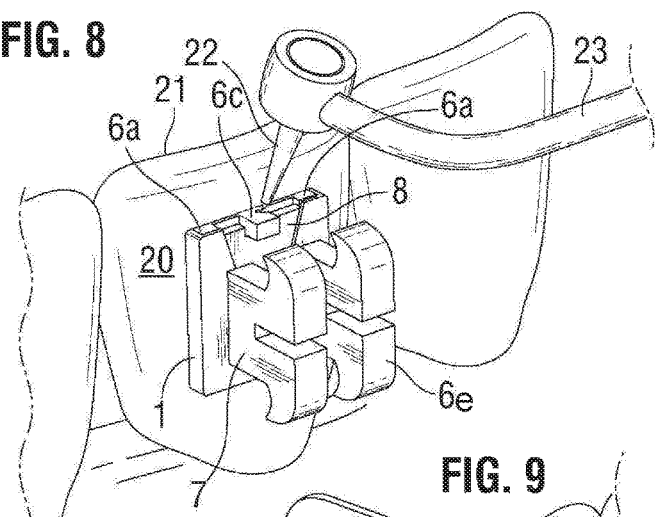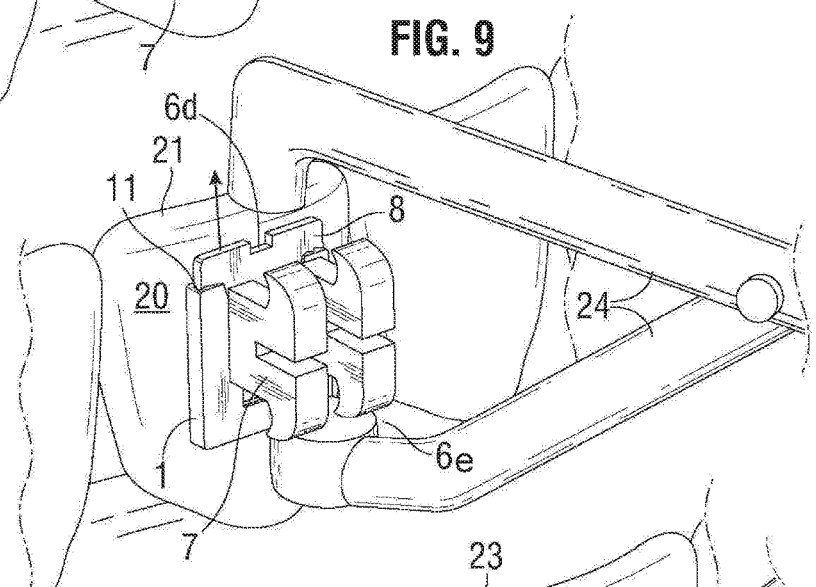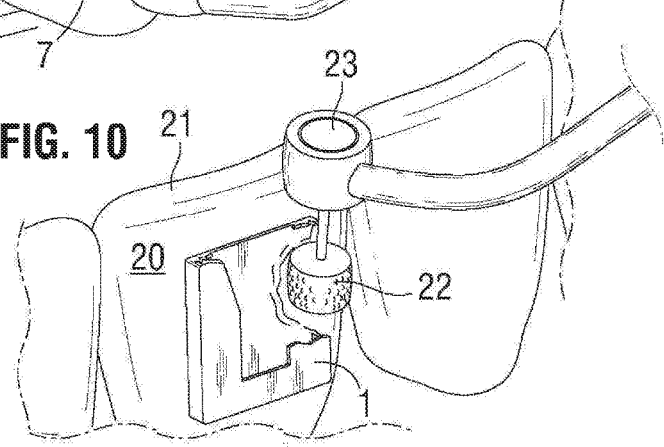

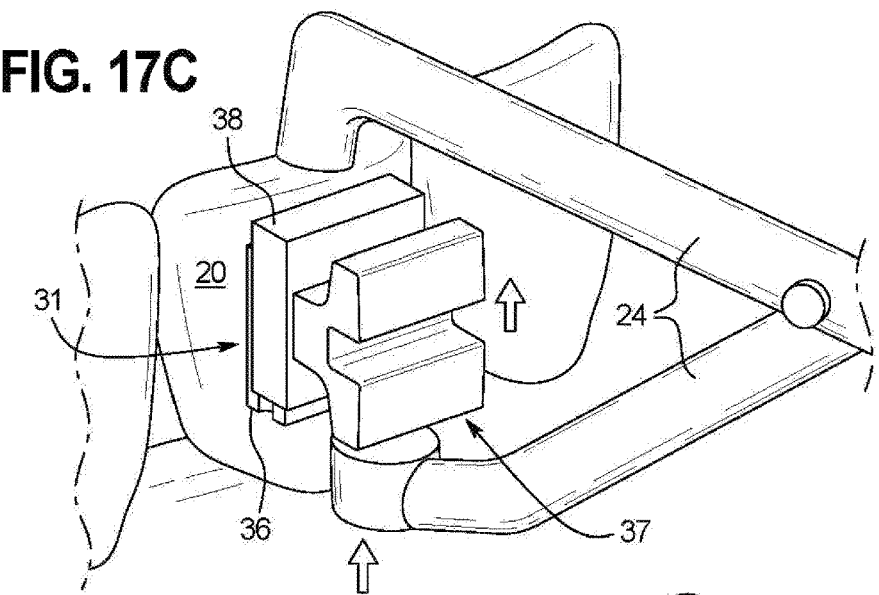
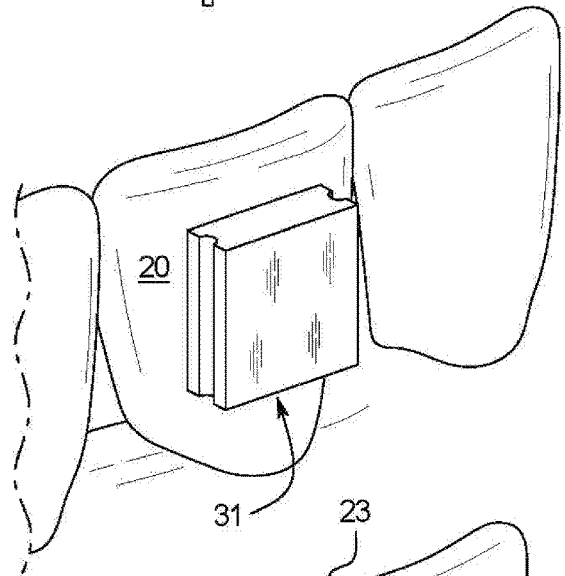
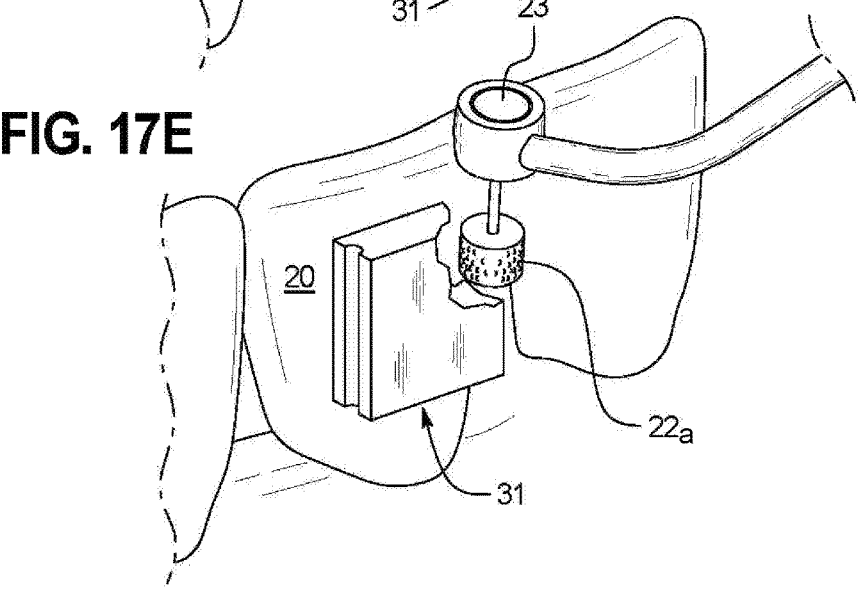

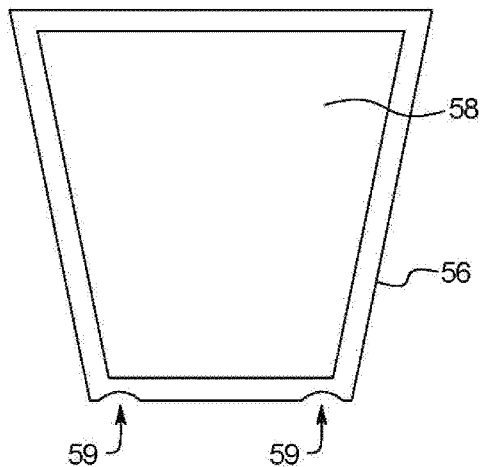
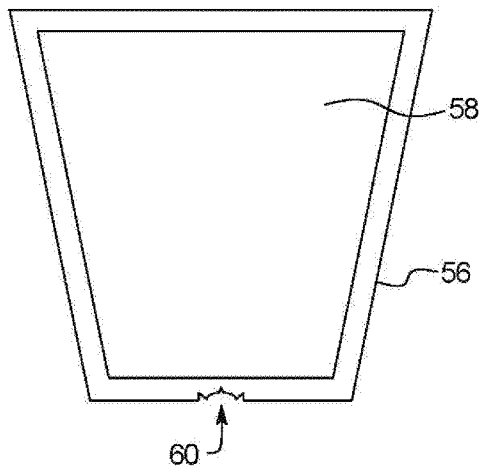
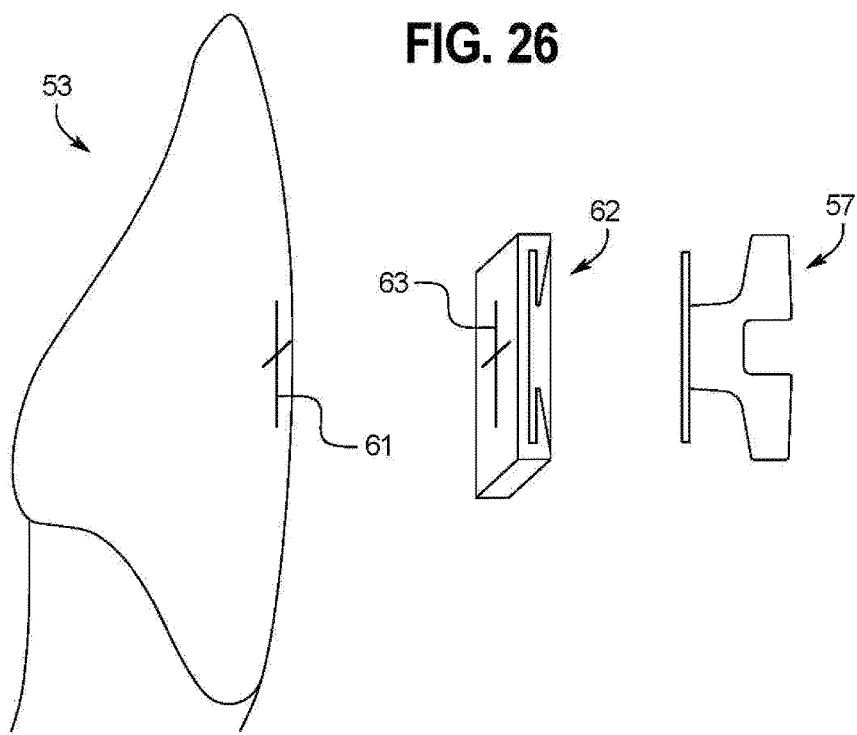

POCKET ORTHODONTIC BONDING PAD

This application is a divisional of U.S. patent application Ser. No. 14/738,748, filed Jun. 12, 2015, which claims the benefit of U.S. Provisional Application No. 62/011,423, filed Jun. 12, 2014. The disclosure of these prior application are hereby incorporated by reference herein in their entireties for all purposes.

This invention relates in general to a polymer/plastic pocket orthodontic bonding pad for orthodontic attachments, mainly brackets. The pocket orthodontic bonding pad removably receives the orthodontic attachment which is locked into the pocket. Upon removal of the lock, the orthodontic attachment is removed with minimal pressure. This is particularly advantageous for orthodontic brackets, which tend to break upon removal. The pocket orthodontic bonding pad imparts a slight degree of flexibility to the orthodontic attachment, which buffers against masticatory forces. The pocket orthodontic bonding pad further allows maximum-strength bonding materials bonding to the tooth, wherein the bonding pad is designed to be the breakaway force determinant for the orthodontic attachment, this force being less than the force being necessary to break tooth enamel from a tooth. This is particularly advantageous because direct bracket/enamel bonds universally create microfractures in enamel when removed or debonded from teeth.

BACKGROUND OF THE INVENTION

With the development of the ability to bond material to teeth, more particularly to tooth enamel, orthodontics was presented with bondable brackets and attachments. The strength of the bracket bond to a tooth was determined by the combination of the strength of the bond to the tooth, the strength of the bonding material, and the strength of the bond to the orthodontic attachment. The bond to the orthodontic bracket was facilitated by using bonding materials, such as acrylics, which readily formed a strong union with the bracket. Metal brackets and other attachments were developed with a mesh-type bonding surface that produced a semi-mechanical lock with the bonding material. Plastic brackets were easily broken and absorbed stains. Ceramic brackets were then developed.

Ceramic brackets, as described in U.S. Pat. No. 4,948,366, were made from mono-crystalline or poly-crystalline aluminum oxide, which were resistant to staining. The bonding surface of the ceramic bracket was treated with a silane coupling agent in order to enhance the strength of the bond with the bonding material. The ceramic material was similar to a diamond, hard and brittle, resulting in a surface hardness greater than that of tooth enamel If the ceramic bracket had an occlusal interference it would abrade the enamel of the opposing teeth. The orthodontic company rushed to market with this new product by advertising directly to the public, which created a public demand for the product before adequate clinical trials had been performed. Clinically, the orthodontist found that when attempting to remove the ceramic bracket from a patient's tooth, the tooth enamel would occasionally detach with the ceramic bracket. The strength of the ceramic bracket to enamel bond was greater than the enamel to the underlying tooth. Research revealed that the smooth bonding surface of the ceramic bracket treated with a silane-coupler greatly enhanced the attachment of the bonding material to the ceramic bracket. It was also found that this type of flat surface on the ceramic bracket produced a very thin layer of bonding film, which in turn produced a stronger bond. The thinner the bonding film the stronger the bond.

Ceramic brackets are often removed with the jaws of an orthodontic pin cutter by placing the cutting edges between the bracket base and the tooth and squeezing. The orthodontic ceramic bracket would often fracture upon attempted removal from the tooth, leaving a piece of the ceramic bracket still bonded to the tooth. At this point a dental drill would often have to be used to remove the piece of ceramic bracket from the tooth. The dental drill was not a perfect solution due to the nature of the hardness of the porcelain bracket. The dental drill most commonly used was diamond-coated, which had close to the same hardness as the porcelain bracket, and which was harder than tooth enamel. The ceramic bracket was also the same color as tooth enamel Thus, tooth enamel could be inadvertently removed.

The mesh-backed metal brackets were more successful than the ceramic bracket. The mesh-backed metal bracket produced a greater thickness of bonding material, allowing enough space between the bracket and the tooth to allow the pin cutter to more easily wedge between the bracket and tooth and remove the bracket when the pin cutter jaws were squeezed together. The metal brackets would not fracture as the porcelain brackets did. The early metal brackets also had the ability to flex, wherein twin brackets could be gripped and squeezed by a pair of pliers, which broke the bond. Modernly, metal brackets are formed by metal injection molding and do not possess this flexing ability yet still will remain in one piece during removal.

Several attempts have been made to solve the debonding problem associated with ceramic brackets. For example, it was proposed in U.S. Pat. No. 4,455,138 that applying heat to the dental bracket would assist in loosening the adhesive bonding of the bracket to the tooth so that the ceramic bracket may be more easily removed with less force. It was found that this system was not always practical as the orthodontist may prematurely pull the bracket in anticipation of the loosening of adhesive, causing great pain to the patient and also shattering the bracket before the heat applied would loosen the adhesive. Further, the pulling force could not be directionally controlled with this system. In addition, the high temperatures associated with this method of removal could cause pulpal or nerve damage to the tooth.

Another debracketing tool and method of removal is disclosed in U.S. Pat. No. 4,907,965, where the heat and debracketing force is simultaneously applied. This system does not always assure that the adhesive is sufficiently loose to allow easy removal, and likewise requires engagement of the ceramic bracket during removal. In addition, the high temperatures associated with this method of removal could cause pulpal or nerve damage to the tooth.

A relatively flexible bonding pad is described in U.S. Pat. No. 5,098,288, wherein a bonding pad is secured to the bracket and bonded to the surface of a tooth. The attached pad is gripped by pliers, causing a buckling of the pad, breaking the bond between the pad and the tooth. The purpose was to prevent fracturing of the bracket during the removal process. However, the flexibility of the bonding pad does not allow for higher bonding strengths between the bonding pad and the enamel surface. In fact, increasing bonding strengths between the bonding pad and the enamel surface decreases flexibility of the bonding pad.

U.S. Pat. No. 5,263,859 describes a flexible bonding pad with holes, allowing the bonding material to come in direct contact with the bracket. The purpose was to increase the strength of the bond to the bracket. However, the flexibility of the bonding pad does not allow for efficient bonding strengths between the bonding pad and the enamel surface. In fact, increasing bonding strengths between the bonding pad and the enamel surface decreases flexibility of the bonding pad.

U.S. Pat. No. 6,786,720 discloses a light-curable methacrylate-based epoxy resin bonding pad molded to a ceramic orthodontic appliance. Debonding is performed by squeezing the pad with ligature cutters, causing the bracket to release from the tooth. However, the flexibility of the bonding pad does not allow for efficient bonding strengths between the bonding pad and the enamel surface. In fact, increasing bonding strengths between the bonding pad and the enamel surface decreases flexibility of the bonding pad.

Another factor involving orthodontic brackets is the unintentional debonding during the patient's treatment which is time-consuming for the orthodontist, and often delays the completion of the patient's treatment. Most commonly, the patient has eaten something too hard. Orthodontics is moving toward digitally-assisted bracket placement. If one failure occurs in treatment, it is virtually impossible to replace the bracket in the same position. With the trend in extended appointment intervals (from traditional 4-week intervals to current 8-10-week intervals), a broken bracket can greatly add additional treatment time and significant cost to the orthodontist due to the process involved to repair the unintentionally broken bond. The dilemma is that orthodontic bond strengths must be strong enough to adhere brackets to teeth yet weak enough that upon removal they do not fracture enamel, causing damage to the teeth. Further, the pulling force could not be directionally controlled with this system.

U.S. Pat. No. 7,819,660 discloses appliances that are not designed to resist or distribute masticatory shear forces of an occlusal gingival direction. The appliances rely on an expensive multitude of bracket bodies with different x-axis, y-axis, and z-axis positions.

Another debracketing tool and method of removal is disclosed in U.S. Pat. No. 4,907,965, wherein heat and debracketing force is simultaneously applied. This system does not always assure that the adhesive is sufficiently loose to allow easy removal, and likewise requires engagement of the ceramic bracket during removal. In addition, the high temperatures associated with this method of removal could cause pulpal or nerve damage to the tooth.

It is also known to provide a relatively flexible bonding pad or base for an orthodontic bracket to facilitate debonding, as disclosed in U.S. Pat. No. 5,098,288. However, it has been found that the bonding between the pad and the bracket often fails during treatment due to the various forces on the bracket during treatment, thereby necessitating re-bonding. Further, the flexibility of the bonding pad does not allow for efficient bonding strengths between the bonding pad and the enamel surface. In fact, increasing bonding strengths between the bonding pad and the enamel surface decreases flexibility of the bonding pad. In such instances, treatment has been interrupted, delaying the ultimate conclusion of treatment, and costly chair time is required to re-bond the bracket to the tooth.

SUMMARY OF THE INVENTION

Orthodontics is moving toward digitally-assisted bracket placement. If one failure occurs in treatment, it is virtually impossible to replace the bracket in the same position. With the trend in extended appointment intervals (from traditional 4-week intervals to current 8-10-week intervals) a broken bracket can greatly add additional treatment time. The dilemma is that orthodontic bond strengths must be strong enough to adhere brackets to teeth yet weak enough that upon removal they do not fracture enamel or damage teeth.

Tavas and Watts reported that shear/peel strengths of bonded adhesives should develop 3.9 to 5.9 MPa. While this relatively weak bond strength ensures easy removal of brackets, it also leaves the patient very susceptible to broken brackets through normal masticatory forces or not adhering to a brace-friendly diet. Literature reports bond strengths to 15 MPa with orthodontic adhesives. Enamel bond strengths of up to 38.3 MPa are currently possible with modern dental materials and it would follow that higher bond strengths will continue to evolve as time goes on. By increasing bond strengths, orthodontic appliances need not rely on surface area for bond strength, permitting orthodontic appliances to be much smaller. Smaller orthodontic appliances are particularly advantageous to dental aesthetics, comfort, and access for hygiene.

Brackets tend to debond through masticatory shear forces in an occlusal gingival direction. Therefore, a bracket that is resistant to this force vector and shock-absorbing to this force vector would be desired. Slight flexibility of the bonding pad tends to mitigate the effects of these shear forces. Current debonding techniques require the orthodontist to remove adhesive remnants from the teeth using a fine fluted finishing bur. Most adhesive remains on the teeth, so it is normal protocol and procedure that this removal process is common. The bonding pads of the present invention and adhesive can be limitless in mechanical and chemical adhesion to teeth, while negating debonding forces to remove bonding pads from teeth. Further, the bonding pads of the present invention are thin and easily destructible, further providing for easy removal.

The concept of the bonding pad is to (1) enable very high bond strength at the pad-enamel interface (chemical/etch retention) through a polymeric/plastic bonding pad that is mechanically attached to the attachment body; (2) enable the orthodontist to remove attachments at very low forces due to the unique design of the bonding pad/attachment interface, such that with a simple adjustment to the bonding pad, mechanical retention of the orthodontic attachment body to the bonding pad is reduced from high strength to near zero; and (3) design the bonding pad/attachment to allow shock absorption to distribute masticatory force. The occlusal-gingival, mesial-distal, and lingual-labial positions are made within the bonding pad's shape, but permit the use of a singular, standard attachment body, which tends to be the expensive and intricate component, especially with the advent of self-ligating orthodontic brackets that have multiple moving parts. The bonding pads are particularly suited to be individually fabricated, preferably specifically to the anatomy of each tooth of a patient, preferably specifically to the occlusal-gingival, mesial-distal, and lingual-labial positions on each tooth of a patient, and preferably printed by a three-dimensional printer.

The present invention enables the orthodontist to lower the forces at the debond appointment by a simple manipulation of the amount of mechanical retention of the orthodontic attachment to the bonding pad. A metal, ceramic, or polymer orthodontic attachment with a smooth base surface can be preferably shaped such that the gingival side is optionally narrow and tapers to a wider occlusal side. Alternatively, the metal, ceramic, or polymer orthodontic attachment with a smooth base surface can be preferably shaped such that the occlusal side is optionally narrow and tapers to a wider gingival side. In alternative embodiments, either of the left and right sides may be optionally narrow and tapered relative to the other. This preferable tapering ensures an easy path of draw in an occlusal direction. Optimal, preferable occlusal or gingival tapering also ensures resistance from an occlusal-gingival direction. The orthodontic attachment is enveloped mechanically in the bonding pad. The bonding pad can optionally be made out of a plastic or polymer that is similar to the bonding adhesives. Further, the bracket cannot be removed from the bonding pad unless the pad is destroyed by removal of locking features, thus creating an irreversible assembly for a more solid structure. This is particularly advantageous because reusable orthodontic bracket assemblies must balance the strength of bonding that permits bracket assembly removal and subsequent reattachment to a patient's tooth with the strength of bonding that prevents accidental dislodgement. The bonding pad of the present invention does not rely on flexibility to debond the attachment; instead, a rotary instrument is used to polish. Further, addition of an orthodontic attachment to the bonding pad adds rigidity to the bonding pad by acting as an underlying framework to support the bonding pad. The polymer mesh could optionally be impregnated with an anti-cariogenic or naturally occurring molecule with the ability to release calcium and phosphate ions, stabilize, and/or mitigate the common occurrence of enamel decalcification that is common around orthodontic bonding pads, such as fluoride, selenium, calcium, casein phosphopeptide ("CPP"), or amorphous calcium phosphate ("ACP").

During debonding of the present invention, no shear forces or compressive forces need be applied to the interface between the bonding pad and tooth enamel Instead, the mechanical tab securing the orthodontic attachment or in the retentive aspects of the bonding pad is removed or polished away. Subsequently, a pliers or debonding tool engages the orthodontic attachment and lifts the attachment out of the pocket of the bonding pad in a gingival to occlusal direction. This debonding procedure eliminates the need to apply a prying or pulling force directly to the interface between the enamel and the bonding pad or orthodontic attachment, mitigating the enamel microfracture damage that occurs to tooth enamel during the typical debonding process.

BRIEF DESCRIPTION OF THE DRAWINGS

FIG. 8 is a perspective view of the pad wherein the attachment-containing pad is attached to a tooth and a dental drill is used to remove the protruding surfaces.

FIG. 9 is a perspective view showing an orthodontic band remover removing the orthodontic attachment from the bonding pad.

FIG. 10 is a perspective view showing a dental handpiece with a grinding stone removing the bonding pad from the surface of the tooth.

FIG. 17C is a perspective view showing an orthodontic band remover removing the orthodontic attachment from the bonding pad in FIG. 17A.

FIG. 17D is a perspective view showing the bonding pad of FIG. 17A after the protruding surface has been removed and the orthodontic attachment lifted off.

FIG. 17E shows showing a dental handpiece with a grinding stone removing the bonding pad of FIG. 17D from the surface of the tooth.

FIG. 24 is a back view of an embodiment of an orthodontic bonding pad that has received an orthodontic attachment.

FIG. 25 is a back view of an alternative embodiment of the orthodontic bonding pad shown in FIG. 24.

FIG. 26 is a perspective view of an alternative embodiment of the tooth shown in FIG. 23.

DETAILED DESCRIPTION OF THE EMBODIMENTS

The present invention relates to an orthodontic attachment bonding pad that contains retentive aspects that receive an orthodontic attachment and has a bonding surface that bonds to a tooth. The design of the pocket is to allow the removal of the attachment with minimal pressure. The pocket orthodontic bonding pad is comprised of a polymer/plastic material that is comprised of a highly bondable material that is of a hardness such that it can be easily removed from a tooth with a dental drill. The material and the design of the pocket orthodontic bonding pad are intended to produce a shock absorbing effect. The x-, y-, and z-directional axes are subsequently referred to and claimed by reference to mesial-distal, occlusal-gingival, and lingual-labial axes for relation to human anatomical dimensions, without respect to corresponding axes; no representation is made, for example, that the x-axis need be limited to specifically correspond to one of mesial-distal, occlusal-gingival, or lingual-labial over either of the others two. Additionally, "torque" refers to the rotation of a tooth on its long axis, especially the movement of the apical portions of the teeth by use of orthodontic appliances. "Angulation" refers to the deviation of a tooth from a straight line, i.e. an occlusal-gingival axis. "Tipping" refers to forcibly pivoting a tooth so that its crown is moved labially or lingually.

Figure 1A:
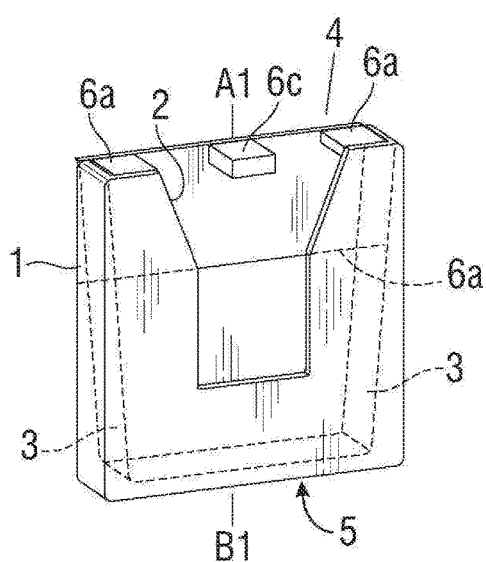
FIG. 1A is a perspective view of the pocket orthodontic bonding pad.

FIG. 1A shows an embodiment of the pocket orthodontic bonding pad 1 with retentive aspects consisting of an internal pocket 2 defined by optionally tapered sides 3 and a top occlusal side 4 and lower gingival side 5. The top occlusal side 4 partially or fully encloses the internal pocket 2 with one or more locking tabs 6a.

Figure 1B:
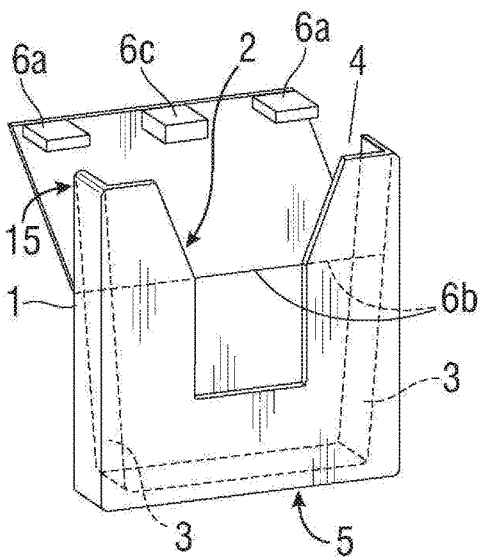
FIG. 1B is a perspective view of the pocket orthodontic bonding pad with the upper part hinged open.

FIG. 1B shows an embodiment of the pocket orthodontic bonding pad 1 wherein the back of the pad 15 is tipped to open at the top occlusal side 4 of the internal pocket 2, hinged by the living hinge 6b. The top occlusal side 4 faces the chewing surfaces of the teeth. The top occlusal side 4 also contains a male surface 6c that protrudes into the internal pocket 2 area. Once the pocket orthodontic bonding pad 1 is closed and is bonded to the enamel surface of a patient's tooth, the living hinge 6b is irreversibly closed over an orthodontic attachment due to the contact with the enamel surface of a patient's tooth, and the orthodontic attachment is retained in the internal pocket 2 until the male surface 6c or top occlusal side 4 is removed. Brackets tend to debond from masticatory shear forces from the occlusal direction because there is no shock-absorbing effect to the enamel/bonding pad interface.

Figure 2:
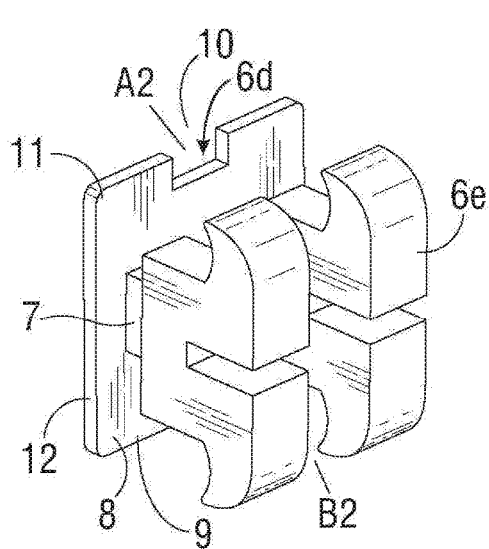
FIG. 2 is a perspective view of an orthodontic attachment with a female receptacle in the base.

FIG. 2 shows an embodiment of an orthodontic attachment 6e with a stem 7 attached to a base 8. The base 8 has a bottom gingival side, 9, an upper occlusal side 11, and left and right sides 12. The left and right sides 12 may optionally be tapered, and widen towards the upper occlusal side 11. Alternatively, the left and right sides 12 may optionally be tapered, and widen towards the bottom gingival side 9. The orthodontic attachment 6e of FIG. 2 inserts within the internal pocket 2 of FIG. 1A wherein A1 aligns with A2 and B1 aligns with B2.

Figure 3:
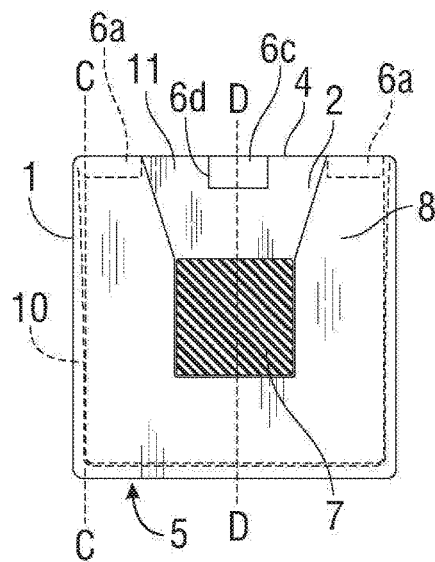
FIG. 3 is a frontal view of the orthodontic attachment stem wherein the base is locked within the pocket orthodontic bonding pad with protruding surfaces and a central protruding surface.

FIG. 3 shows the base 8 within the internal pocket 2, the stem 7 centrally, and the male surface 6c seated within the female receptacle 6d. The male surface 6c and female receptacle 6d are optional features and neither the pocket orthodontic bonding pads nor orthodontic attachments of the present invention are limited to embodiments including a male surface 6c and/or female receptacle 6d.

Figure 4:
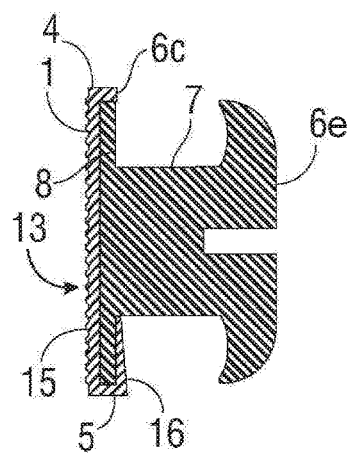
FIG. 4 is a cross-section of FIG. 3 through D-D showing a cross-section of the orthodontic bracket.

FIG. 4 shows a cross-section through D-D of FIG. 3. A male surface 6c locks the base 8. The bonding surface 13 of the pocket orthodontic bonding pad 1 is irregular, which enhances the strength of the bond. Because the pocket orthodontic bonding pad 1 is not forcibly removed from a tooth, but instead polished off of a tooth, the irregularity of the bonding surface 13 is limitless, thus enhancing the mechanical retention of the adhesive to the bonding pad.

Figure 5:
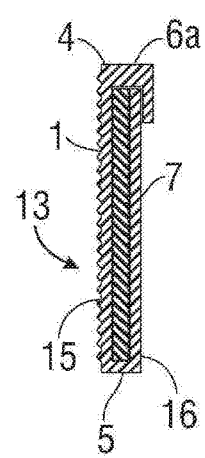
FIG. 5 is a cross-section of FIG. 3 through C-C.

FIG. 5 is a cross-section of FIG. 3 through C-C. The top occlusal side 4 of the pocket orthodontic bonding pad 1 wherein the locking tabs 6a enclose the base 8. The front side 16 of the pocket orthodontic bonding pad 1 completes the enclosure of the base 8. It is desirable that the pocket orthodontic bonding pad 1 have a shock-absorbing effect in order to resist the chewing forces. The shock-absorbing effect is determined by the material and the design of the pocket orthodontic bonding pad 1. The break-away release force of the orthodontic attachment 6e is the force required to dislodge the orthodontic attachment 6e from the pocket orthodontic bonding pad 1. The break-away force is determined by the locking tabs 6a or top occlusal side 4, the optional male surface 6c engaging the optional female receptacle 6d or upper occlusal side 11 of the base 8, and the front of the pocket orthodontic bonding pad 1. It is important that the break-away force to intentionally release the attachment from the bonding pad is less than the force to remove enamel from a tooth. The ability to keep the orthodontic attachment 6e on a tooth is only compromised when the locking tabs 6a, top occlusal side 4, or male surface 6c is removed. Conversely, it is important that the retention force be great enough to retain the orthodontic attachment 6e for the duration of the treatment. Besides being time-consuming to replace an orthodontic attachment 6e, modern orthodontics is turning to computer-positioned attachments and 8-10 week appointment intervals, where it is virtually impossible to replace an attachment in its original computer-selected position.

Figure 6:
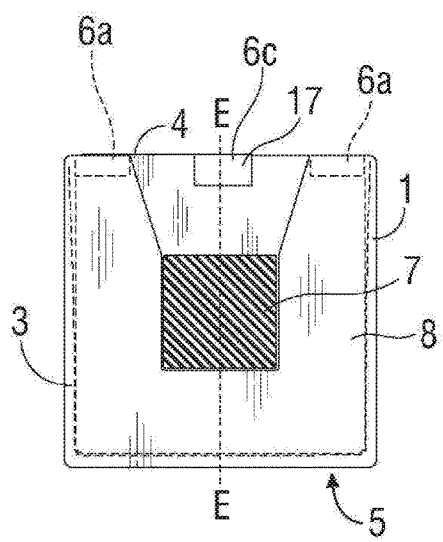
FIG. 6 is a frontal view of the orthodontic attachment stem wherein the base is locked within the pocket orthodontic bonding pad with protruding surfaces.
Figure 7:
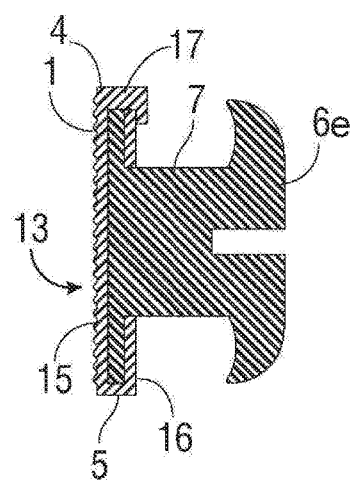
FIG. 7 is a cross-section of FIG. 6 through E-E showing a cross-section of the orthodontic attachment.

FIG. 6 discloses another embodiment wherein the pocket orthodontic bonding pad 1 has a tab 17 at the top occlusal side 4 that encloses the base 8 as shown in FIG. 7.

FIG. 7 shows a cross-section of FIG. 6 through E-E wherein the occlusal portion of the base 8 is enclosed by the tab 17.

FIG. 8 discloses the pocket orthodontic bonding pad 1 bonded to a tooth 20 with the tooth occlusal 21 facing upwards and the pocket orthodontic bonding pad 1 upper occlusal side 11 facing upwards. A dental drill 22 attached to a dental handpiece 23 is used to remove the locking tabs 6a and the male surface 6c. The orthodontic attachment 6e is now open to the upper occlusal side 11. The optionally tapered sides 3 and left and right sides 12, as shown in FIGS. 1, 2, 3, and 6, further facilitate the removal in an occlusal 21 direction with minimal pressure. The orthodontic attachment 6e may be removed without breakage to the orthodontic attachment 6e or tooth 20. This is particularly advantageous for removing attachments, which are prone to breakage during removal. Pieces of a broken bracket left on a tooth frequently have to be ground off, using very aggressive cutting instruments and/or diamonds, which is difficult due to hardness of the material. The grinding process with these aggressive cutting instruments and/or diamonds may also inadvertently remove underlying tooth 20 enamel.

FIG. 9 shows an orthodontic band-removing pliers 24 used to remove the orthodontic attachment 6e from the pocket orthodontic bonding pad 1 in an occlusal 21 direction. This removal requires minimal pressure, which is comfortable for the patient and does not run the risk of breaking the orthodontic attachment 6e. The lack of breakage of the orthodontic attachment 6e is especially advantageous as brackets are very prone to breakage during removal.

FIG. 10 shows a dental handpiece 23 with a polisher 22 removing the remainder of the pocket orthodontic bonding pad 1 from the tooth 20. The pocket orthodontic bonding pad 1 is comprised of a material softer than tooth enamel, which allows easy removal. The pocket orthodontic bonding pad 1 is comprised of a polymer or acrylic, which is firm enough to retain the orthodontic attachment 6e, flexible enough to allow some flexion of the orthodontic attachment 6e, flexible enough to allow some flexion of the orthodontic attachment 6e within the pocket orthodontic bonding pad 1, and soft enough to allow the pocket orthodontic bonding pad 1 to be easily polished off the tooth 20 as shown in FIG. 10.

Figure 11:
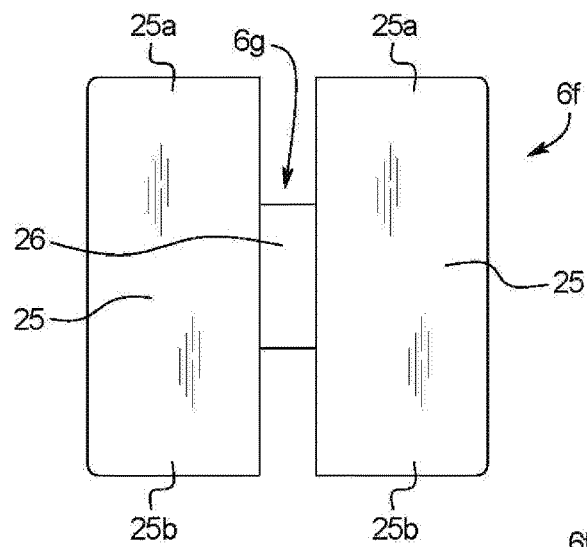
FIG. 11 is a rear view of an orthodontic attachment embodiment with a relief channel
Figure 12:
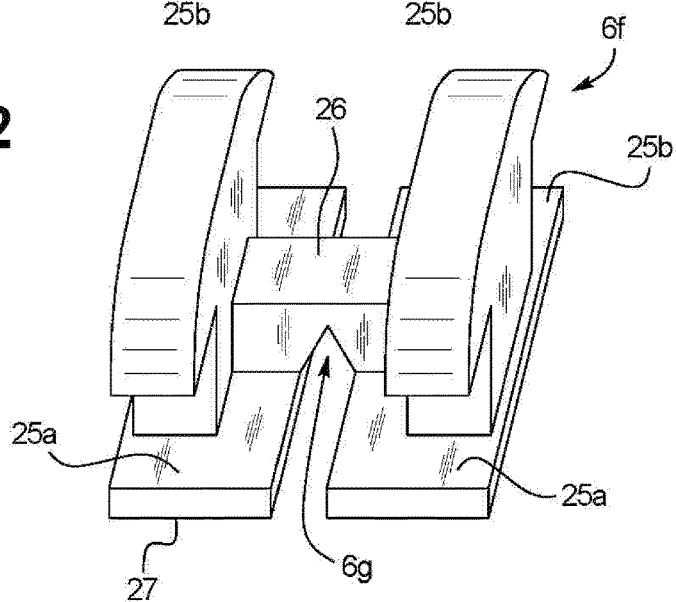
FIG. 12 is a perspective view of the orthodontic attachment shown in FIG. 11.

FIG. 11 shows the rear view of an orthodontic attachment 6f with a stem 26 attached to a base 25 with an upper occlusal side 25a and a lower gingival side 25b. The base 25 is bifurcated along the occlusal-gingival axis, with a relief channel 6g between the halves of the bracket base 25, and extending into the stem 26, as seen in FIG. 12. The base 25 has a smooth outer surface 27.

Figure 13:
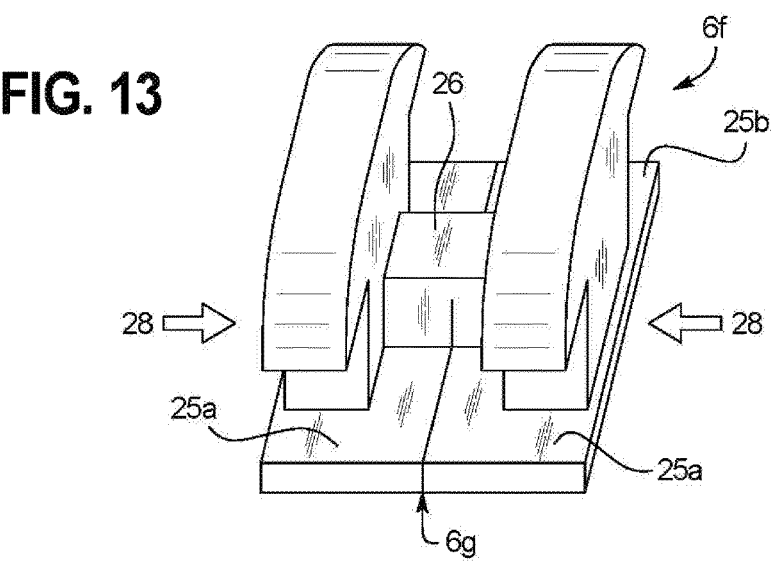
FIG. 13 is a perspective view of the orthodontic attachment with a relief channel with mesial-distal pressure exerted such that the bracket is compressed inward into the relief channel

FIG. 13 is a perspective view of the orthodontic attachment 6f with mesial-distal pressure 28 applied such that the halves of base 25 are compressed inward into the relief channel 6g. The compression allows the orthodontic attachment 6f to be removed from a pocket orthodontic bonding pad with minimal pressure, by removing the periphery of the base from the retentive aspects of the bonding pad.

Figure 14:
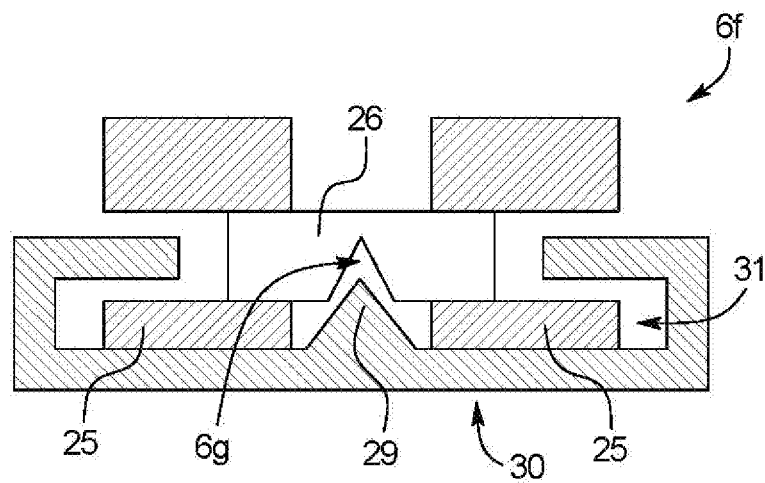
FIG. 14 is a top cross-section view of an orthodontic attachment with a relief channel reversibly received into a pocket orthodontic bonding pad with a spine.

FIG. 14 is a top-cross-section view of an orthodontic attachment 6f with a relief channel 6g reversibly received into a pocket orthodontic bonding pad 30 with a spine 29 and internal pocket 31. The bifurcated halves of the bracket base 25 flank the sides of the spine 29. The spine 29 is an optional feature of pocket orthodontic bonding pad 30 and is by no means intended to limit the presently claimed inventions to the currently described embodiment.

Figure 15:
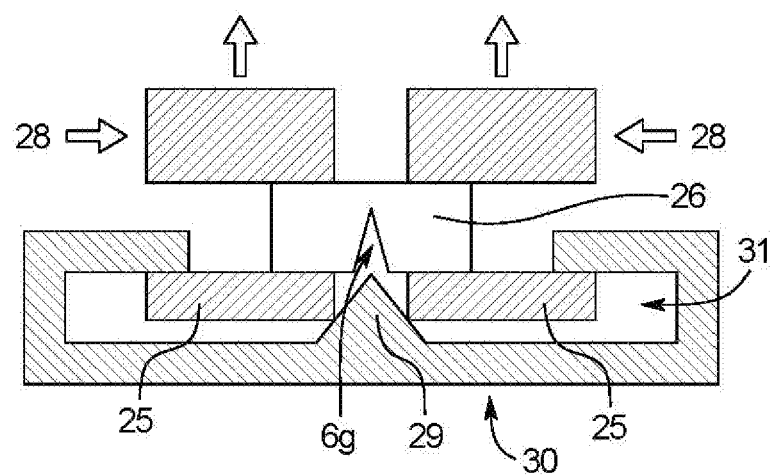
FIG. 15 is a top cross-section view showing application of mesial-distal pressure to an orthodontic attachment with a relief channel reversibly received into a pocket orthodontic bonding pad with a spine.

FIG. 15 shows the application of mesial-distal pressure to an orthodontic attachment 6f reversibly with a relief channel 6g reversibly received into a pocket orthodontic bonding pad 30 with a spine 29. The spine 29 diverts the compressed halves of the base 25 outward away from the pocket orthodontic bonding pad 30, allowing the orthodontic attachment 6f to be removed with minimal pressure. The spine 29 is an optional feature of pocket orthodontic bonding pad 30 and is by no means intended to limit the presently claimed inventions to the currently described embodiment.

Figure 16:
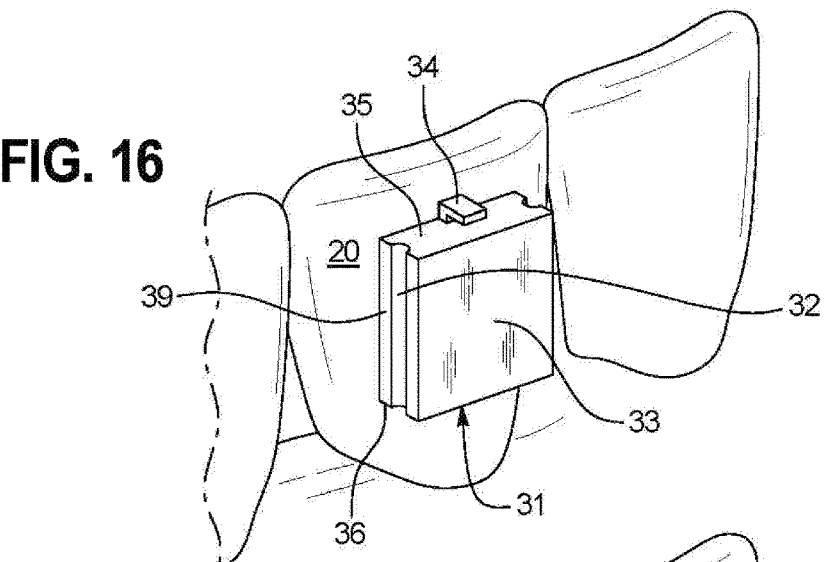
FIG. 16 is a perspective view of an alternative embodiment of an orthodontic bonding pad attached to a tooth.

FIG. 16 is a perspective view of an embodiment of an orthodontic bonding pad 31 bonded to a tooth 20. The orthodontic bonding pad 31 has a top occlusal side 35 and a bottom gingival side 36. The stem 32 is in the shape of a female depression attached to the front of the bonding pad base 39. The head 33 is attached to the end of the stem 32 opposite that attached to the base 39. A protruding surface 34 is attached centrally on the top occlusal side, preferably flush with the bonding surface, and can lock an orthodontic attachment received by the orthodontic bonding pad 31 in place until the protruding surface 34 is removed.

Figure 17A:
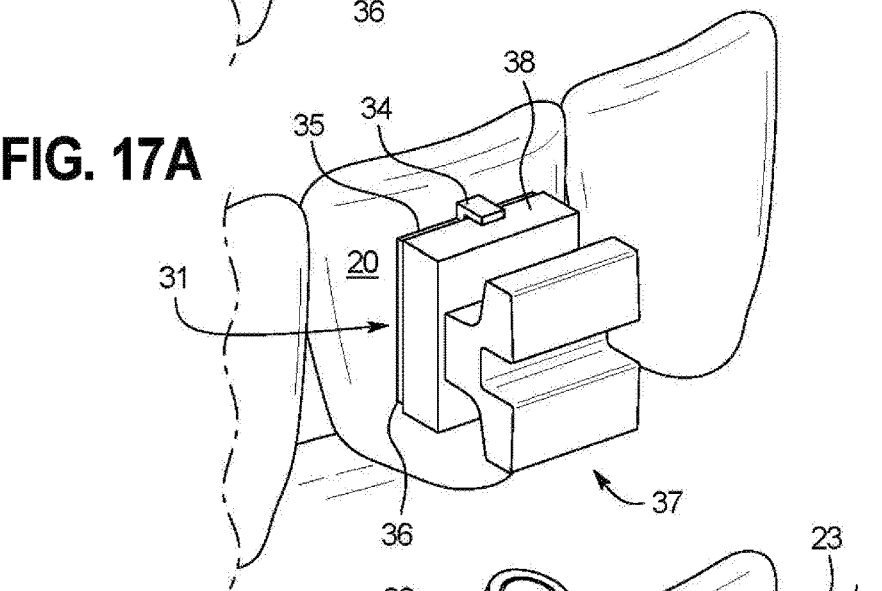
FIG. 17A is a perspective view of an orthodontic attachment that has reversibly received the orthodontic bonding pad of FIG. 16.
Figure 17B:
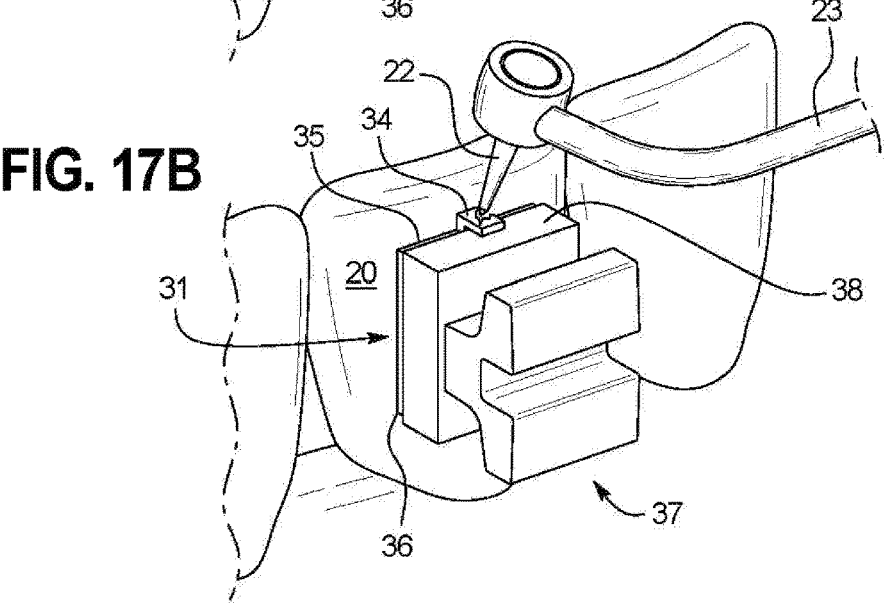
FIG. 17B is a perspective view showing a dental drill removing a protruding surface from the orthodontic bonding pad in FIG. 17A.

FIG. 17A is a perspective view of an embodiment of an orthodontic attachment 37 that has reversibly received the head 33 of the orthodontic bonding pad 31 shown in FIG. 16. The orthodontic attachment has a top occlusal side 38 that is locked in receiving position by protruding surface 34. The orthodontic attachment 37 cannot be removed from the orthodontic bonding pad 31 until the male tab 34 on the orthodontic bonding pad 31 has been removed. FIG. 17B shows a dental handpiece 23 with a drill 22 removing the protruding surface 34 from orthodontic bonding pad 31. The orthodontic attachment 6e may be removed without breakage to the orthodontic attachment 37 or tooth 20. This is particularly advantageous for removing attachments, which are prone to breakage during removal. Pieces of a broken bracket left on a tooth frequently have to be ground off, using very aggressive cutting instruments and/or diamonds, which is difficult due to hardness of the material. The grinding process, using very aggressive cutting instruments and/or diamonds, may also inadvertently remove underlying tooth 20 enamel FIG. 17C shows an orthodontic band-removing pliers 24 used to remove the orthodontic attachment 37 from the pocket orthodontic bonding pad 31 in an occlusal direction. This removal requires minimal pressure, which is comfortable for the patient and does not run the risk of breaking the orthodontic attachment 37. The lack of breakage of the orthodontic attachment 37 is especially advantageous as brackets are very prone to breakage during removal. FIG. 17D shows the orthodontic bonding pad 31 after the orthodontic attachment 37 has been removed. The protruding surface 34 in FIG. 16 had to be removed in order to remove the orthodontic attachment 37. FIG. 17E shows a dental handpiece 23 with a polisher 22a removing the remainder of the orthodontic bonding pad 31 from the tooth 20. The pocket orthodontic bonding pad 31 is comprised of a material softer than tooth enamel, which allows easy removal. The orthodontic bonding pad 31 is comprised of a polymer or acrylic, which is firm enough to be locked in the orthodontic attachment 37, flexible enough to allow some flexion of the orthodontic attachment 37 around the orthodontic bonding pad 31, and soft enough to allow the orthodontic bonding pad 31 to be easily polished off the tooth 20. The orthodontic bonding pad 31 and orthodontic attachment 37 may each be optionally tapered to the occlusal or gingival for resistance from and path of draw in removal.

Figure 18A:
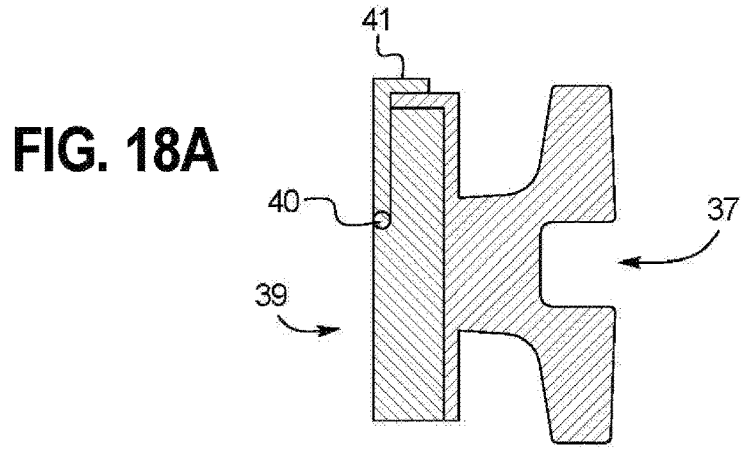
FIG. 18A is an occlusal-gingival cross-section of an alternative embodiment of an orthodontic bonding pad with a living hinge that has been reversibly received by an orthodontic attachment.
Figure 18B:
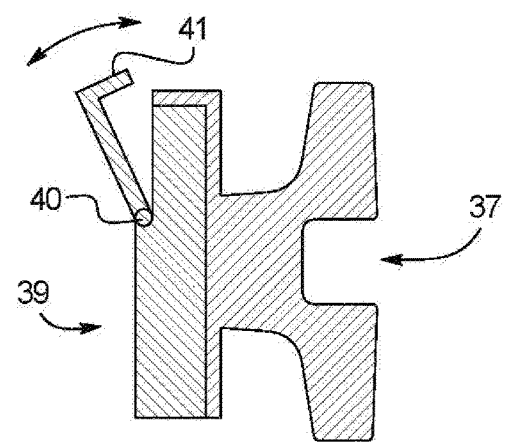
FIG. 18B is an occlusal-gingival cross-section showing the movement of the orthodontic bonding pad of FIG. 18A when open, the bonding surface of the orthodontic bonding pad not bonded to the enamel of a tooth.
Figure 18C:
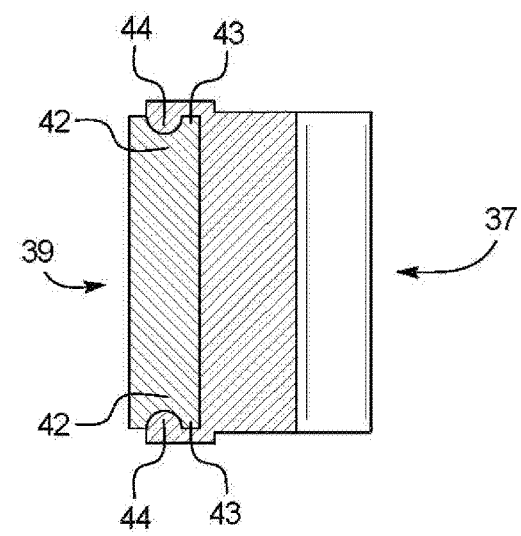
FIG. 18C is a mesial-distal cross-section of the orthodontic attachment in FIG. 18A that has reversibly received the orthodontic bonding pad.

FIG. 18A shows an occlusal-gingival cross-section of the orthodontic bonding pad 39 that has reversibly received an orthodontic attachment. The bonding surface has a a mesial-distal living hinge 40 on the bonding surface such that the top occlusal side and protruding surface 41 can reversibly engage the upper occlusal side of an orthodontic attachment 37, and the living hinge 40 is locked, and cannot be opened, upon bonding of the bonding surface of the orthodontic bonding pad 39 to the enamel of a tooth such that the head of the orthodontic bonding pad 39 is locked inside the retentive aspects of the orthodontic attachment 37 until the protruding surface 41 is removed. FIG. 18B shows the movement of living hinge 40 of FIG. 18A when the bonding surface of orthodontic bonding pad 39 is not bonded to the enamel of a tooth. Orthodontic attachment 37 can reversibly receive the head of orthodontic bonding pad 39 when the bonding surface of orthodontic bonding pad 39 is not bonded to the enamel of a tooth. FIG. 18C shows a mesial-distal cross-section of the embodiment of FIG. 18A, with the retentive aspects 44, shown here in the form of rails, of the orthodontic attachment 37 receiving the head 43 of the orthodontic bonding pad 39 by sliding into the stem 42, shown here in the form of female depressions, of the orthodontic bonding pad 39. The protruding surface 41 is an occlusal aspect of the living hinge 40 on the top occlusal side, and locks the orthodontic attachment 37 in place until the protruding surface 41 or top occlusal side is removed.

Figure 19:
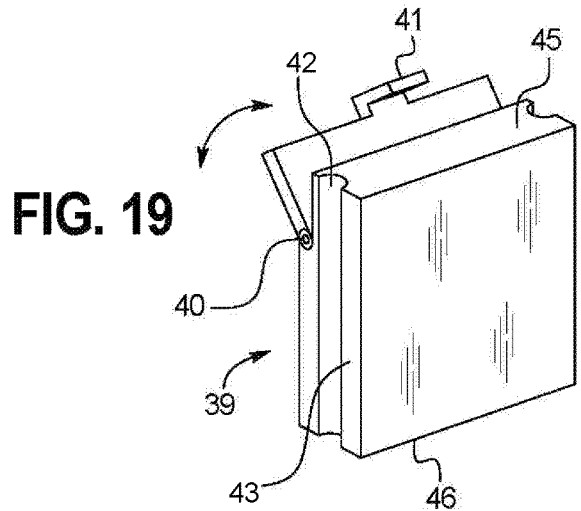
FIG. 19 is a perspective view showing an alternative embodiment of an orthodontic bonding pad with a living hinge on the bonding surface.

FIG. 19 is a perspective view of the orthodontic bonding pad 39 shown in FIGS. 18A, 18B, and 18C. The orthodontic bonding pad 39 has a protruding surface 41 that eclipses the top occlusal side 45 when the living hinge 40 is closed.

Figure 20:
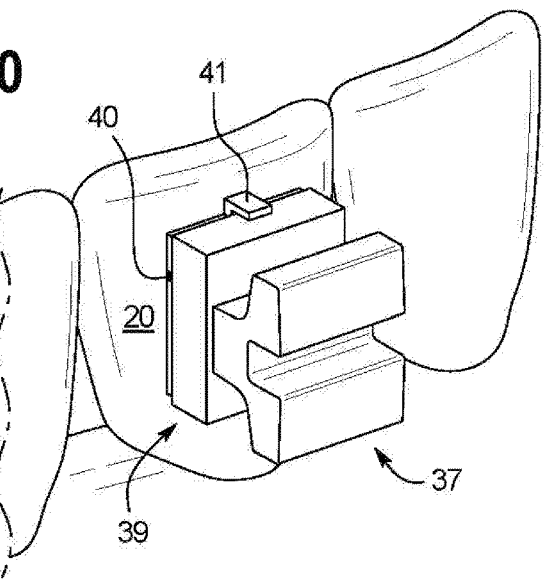
FIG. 20 is a perspective view of an orthodontic attachment that has reversibly received the orthodontic bonding pad of FIG. 19.

FIG. 20 is a perspective view of the orthodontic bonding pad 39 shown in FIG. 19 bonded to a tooth 20, the orthodontic bonding pad 39 locked inside an orthodontic attachment 37 until the protruding surface 41 is removed.

Figure 21:
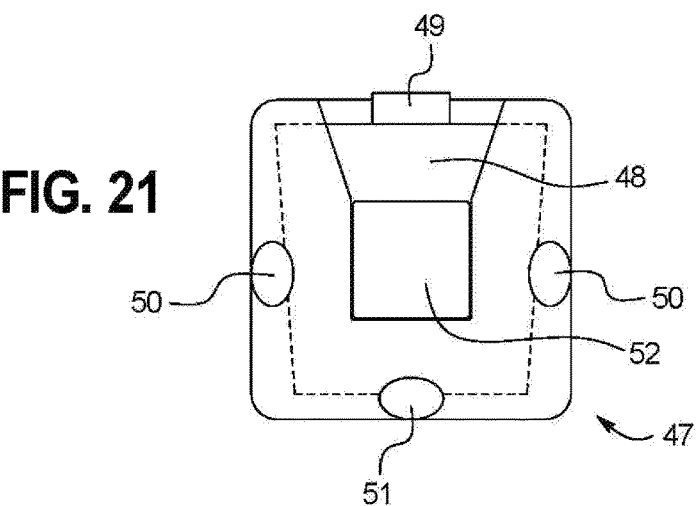
FIG. 21 is a lingual-labial cross-section of an alternative embodiment of an orthodontic bonding pad that has received an orthodontic attachment.

FIG. 21 shows a lingual-labial cross-section view of an orthodontic bonding pad 47 that has received the base 48 of an orthodontic attachment with stem 52. This alternative embodiment has retentive aspects in the form of tab 51 on the bottom gingival side and protruding surface 49 on the top occlusal side, and optional tabs 50 on the left and right sides.

Figure 22:
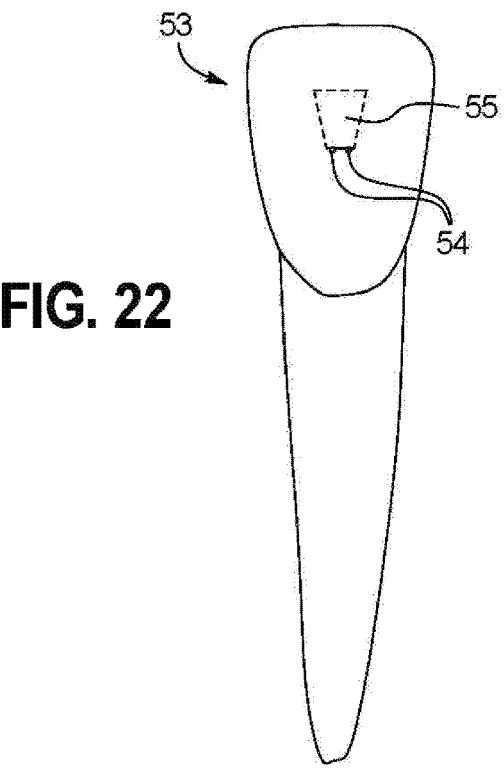
FIG. 22 shows a single tooth of a replica of an individual patient's tooth.

FIG. 22 shows a replica tooth 53, preferably a three-dimensionally printed replica of a patient's tooth. Computer software determines the locations of positional markers 54, which will cooperatively engage an orthodontic bonding pad such that the orthodontic bonding pad is appropriately positioned in the desired location on the tooth 53, as indicated by silhouette 55.

Figure 23:
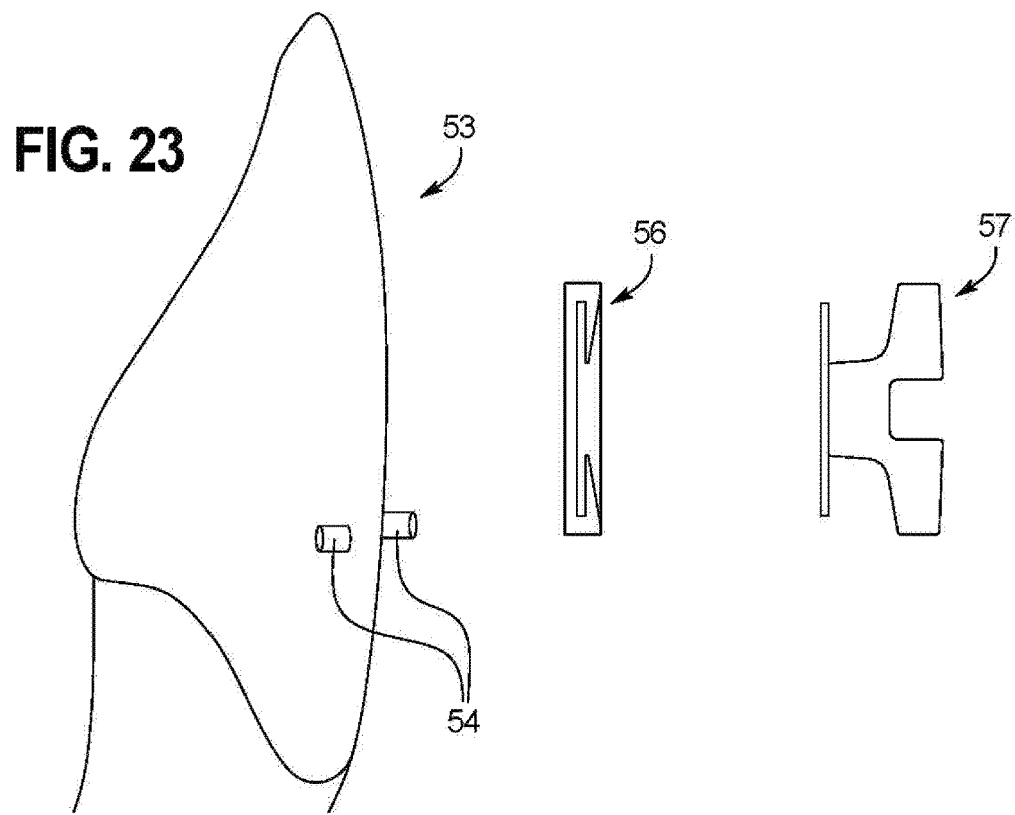
FIG. 23 is a perspective view of the single tooth shown in FIG. 22.

FIG. 23 shows the replica tooth 53 of FIG. 22, with orthodontic bonding pad 56, which will be preferably three-dimensionally printed to cooperatively engage the positional markers 54, and which will reversibly receive orthodontic bonding pad 57.

FIG. 24 shows the back view of the bonding surface of orthodontic bonding pad 56, which has reversibly received orthodontic attachment 58. The bottom gingival side of the orthodontic bonding pad 56 is specifically shaped with notches 59 to cooperatively engage the two positional markers 54 on replica tooth 53. By pre-determining positions of orthodontic bonding pads 56, an orthodontist's assistant can prepare entire upper and lower jaw sets of properly positioned orthodontic bonding pads 56 on printed models, with positional markers 54 of the individual patient's dentition for the fabrication of indirect bonding trays, by matching up positional markers 54 to notches 59. This is particularly advantageous because a doctor need only select positions of orthodontic attachments, and the replica tooth 53 and orthodontic bonding pad 56 are preferably three-dimensionally printed and positioned for quick bonding by an assistant, saving an orthodontist time.

FIG. 25 shows an alternative embodiment of orthodontic bonding pad 56 with a specifically shaped singular bottom gingival side with irregular notch 59, which identically matches the singular positional marker allowing occlusal-gingival, mesial-distal, and lingual-labial positioning of bracket to tooth.

FIG. 26 shows an alternative embodiment to the replica tooth 53 of FIG. 22, wherein a male-projection hash mark 61 is matched to a female similar mark 63 on the orthodontic bonding pad 62 for proper positioning. The advantage of the female similar mark 63 on the orthodontic bonding pad 62 is that it allows a defined hollow in the orthodontic bonding pad 62 to be filled with adhesive, ensuring a very thin coat of adhesive so that there will be minimal adhesive flash to clean up around the periphery of the orthodontic bonding pad 62 and orthodontic attachment 57 once attached. The orthodontic bonding pad 62 can reversibly receive orthodontic attachment 57.

Figure 27:
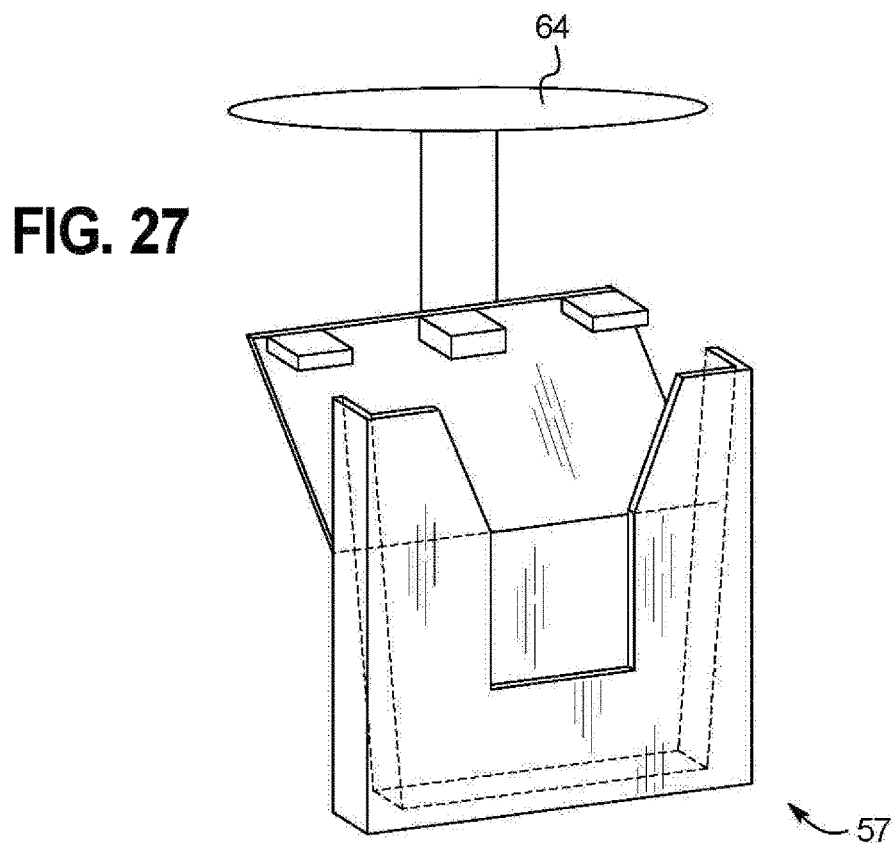
FIG. 27 is a perspective view of an embodiment of an orthodontic bonding pad with an occlusal index attached.

FIG. 27 shows an orthodontic bonding pad 57 with an integrated index 64 attached on the top occlusal side. Ideally, the entire orthodontic bonding pad 57 and integrated index 64 assembly are three-dimensionally-printed in combination with orthodontic bonding pad 57 and integrated index 64 assemblies for an entire upper jaw or lower jaw set. The specific distance and projectional path between the integrated index 64 and the orthodontic bonding pad 57 reflects the calibrated positioning of the orthodontic bonding pad 57 in order to control occlusal-gingival, mesial-distal, and lingual-labial positioning of the orthodontic bonding pad 57 on the patient's tooth. This is particularly advantageous because the anatomy of the tooth is captured in the integrated index 64 such that when the integrated index 64 is applied to the comparable tooth of the patient, the orthodontic bonding pad 57 will be bonded in the pre-selected position. This saves an orthodontist time in positioning orthodontic bonding pad 57 and the need to create a transfer or indirect bonding tray.

Figure 28:
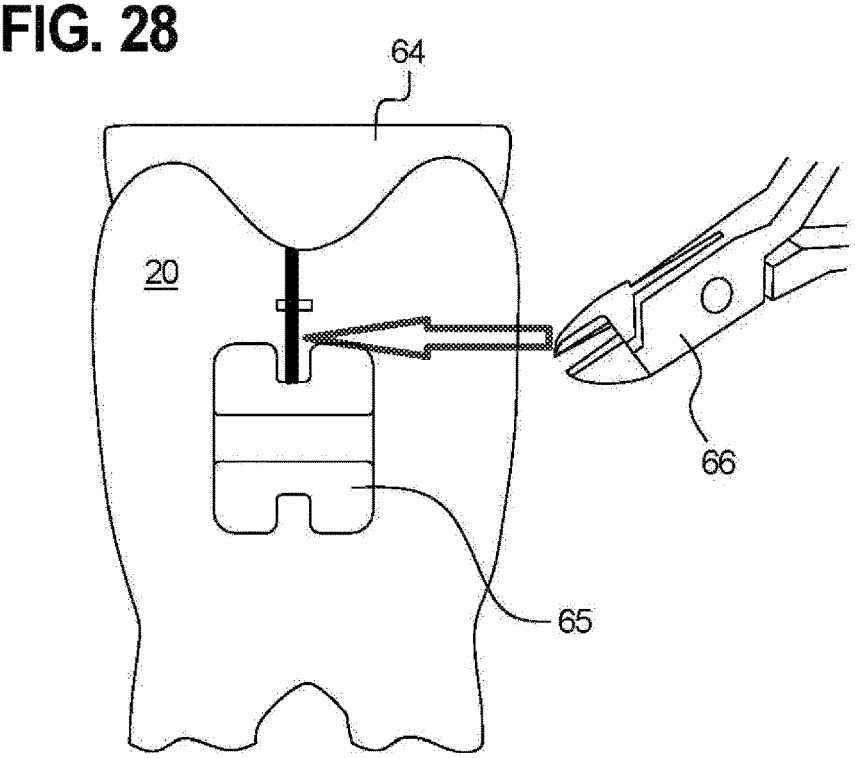
FIG. 28 is a frontal view of a tooth of a patient with the orthodontic bonding pad of FIG. 27 that has reversibly received an orthodontic attachment.

FIG. 28 shows a front view of a patient's tooth 20. The integrated index 64 has cooperatively engaged the occlusal surface of the tooth such that the orthodontic attachment 65, and the orthodontic bonding pad 57 (not shown) that has reversibly received the orthodontic attachment 65, will be placed in the pre-selected position on the tooth 20. Subsequent to bonding, orthodontic device 66 is used to cut the integrated index 64 from the orthodontic bonding pad 57 (not shown).

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of the inventive concept.

I claim:
1. A pocket orthodontic bonding pad, comprising:
   a four-sided pad with a top occlusal side, a bottom gingival side, left and right sides, a front and a back and retentive aspects, wherein the retentive aspects are on the left side, the bottom gingival side, and the right side of the four-sided pad, and the four-sided pad is open to the top occlusal side, and the retentive aspects can receive an orthodontic attachment;
   a male surface located on the top occlusal side, wherein the male surface retains a base of an orthodontic attachment in the retentive aspects during orthodontic treatment;
   a bonding surface on the back of the four-sided pad, wherein the bonding surface is irregular in order to enhance a bonding strength of the bonding surface;
   an integrated index on the top occlusal side of the four-sided pad; and
   a specific distance and projectional path between occlusal end of the integrated index and the four-sided pad;
   wherein the removal of the base of the orthodontic attachment is dependent upon prior removal of the protruding surface or upon prior removal of one of the retentive aspects;
   wherein the back of the four-sided pad comprises a shape comprising specific occlusal-gingival, mesial-distal, and lingual-labial dimensions; and wherein the specific distance and projectional path determine the position of the pocket orthodontic bonding pad on a tooth, and the specific occlusal-gingival, mesial-distal, and lingual-labial dimensions align the orthodontic attachment at a specific, pre-determined occlusal-gingival, mesial-distal, lingual-labial position and torque when the orthodontic attachment base is received by the retentive aspects of the pocket orthodontic bonding pad.

2. A pocket orthodontic bonding pad as in claim 1, wherein the four-sided pad further comprises one or more specifically shaped notches on the bottom gingival side.

3. Positional markers on a replica of a patient's tooth such that the positional markers cooperatively engage the one or more specifically shaped notches on the bottom gingival side of the four-sided pad of the pocket orthodontic bonding pad as in claim 2.

4. A pocket orthodontic bonding pad as in claim 1, further comprising a living hinge on the back of the four-sided pad in a mesial-distal direction, the living hinge allowing the top occlusal side to be opened such that the retentive aspects of the four-sided pad can receive the base of an orthodontic attachment, and wherein the living hinge is irreversibly closed once the bonding surface is attached to a tooth such that the base of the orthodontic attachment is retained in the retentive aspects until one of the retentive aspects or the male surface is removed.

5. A pocket orthodontic bonding pad as in claim 1, wherein at least the bottom gingival side of the four-sided pad further comprises one or more specifically shaped notches such that the one or more specifically shaped notches cooperatively engages pre-determined positional markers on a three-dimensional replica of a patient's tooth corresponding to a pre-determined occlusal-gingival, mesial-distal, lingual-labial position of the patient's tooth, the pocket orthodontic bonding pad subsequently bonded to the enamel of the patient's tooth such that the orthodontic attachment received by the pocket orthodontic bonding pad is aligned at a pre-determined occlusal-gingival, mesial-distal, lingual-labial position and, optionally, can achieved desired torque, angulation, and/or tipping.

6. A pocket orthodontic bonding pad as in claim 1, wherein the retentive aspects on the left and right sides of the four-sided pad taper wider to the occlusal, facilitating removal of the orthodontic attachment to the occlusal following the removal of the male surface using a device such as a dental drill, the removal of the orthodontic attachment with the use of an orthodontic instrument.

7. A pocket orthodontic bonding pad as in claim 1, wherein the retentive aspects on the left and right sides of the four-sided pad taper wider to the gingival, facilitating removal of the orthodontic attachment to the occlusal following the removal of the male surface using a device such as a dental drill, the removal of the orthodontic attachment with the use of an orthodontic instrument.

8. A pocket orthodontic bonding pad as in claim 1, wherein the retentive aspects are a hollow pocket that is enclosed on the left, bottom gingival, and right sides, and open to the top occlusal side, and that can receive the orthodontic attachment.

9. A pocket orthodontic bonding pad as in claim 1, wherein the retentive aspects are tabs on the bottom gingival, and optionally the left and right sides of the four-sided pad, which can receive the orthodontic attachment base.

10. A pocket orthodontic bonding pad as in claim 1, wherein the bonding strength between the bonding surface of the pocket orthodontic bonding pad and an enamel surface of a tooth is at least 12 MPa.

11. A pocket orthodontic bonding pad as in claim 1, further comprising a spine in the middle of the front side of the four-sided pad from the top occlusal side to the bottom gingival side, the spine protruding outward from the four-sided pad of the pocket orthodontic bonding pad, the spine tilling a relief channel in the orthodontic attachment with a relief channel, the orthodontic attachment received in the hollow pocket of the pocket orthodontic bonding pad, and the spine diverting the orthodontic attachment with the relief channel outward or away from the pocket orthodontic bonding pad upon application of mesial-distal pressure to the orthodontic attachment with the relief channel.

12. A pocket orthodontic bonding pad as in claim 1, further comprising a spine in the middle of the front side of the four-sided pad from the left side to the right side, the spine protruding outward from the four-sided pad of the pocket orthodontic bonding pad, the spine filling a relief channel in the orthodontic attachment with a relief channel, the orthodontic attachment received in the hollow pocket of the pocket orthodontic bonding pad, and the spine diverting the orthodontic attachment with the relief channel outward or away from the pocket orthodontic bonding pad upon application of occlusal-gingival pressure to the orthodontic attachment with the relief channel.

13. A pocket orthodontic bonding pad as in claim 1 that is an output of a three-dimensional printing device.

14. A pocket orthodontic bonding pad as in claim 1, wherein the bottom gingival side, left side, or right side, or the bonding surface of the four-sided pad has one or more specifically shaped notches or female marks that individually or together form a unique pattern, and that uniquely and cooperatively engage corresponding positional markers, on a replica of a patient's tooth.

15. Positional markers on a replica of a patient's tooth such that the positional markers cooperatively engage the one or more specifically shaped notches or female marks that are located on the bottom gingival side, left side, or right side, or the bonding surface of the four-sided pad of the pocket orthodontic bonding pad as in claim 14.

* * * * *